United States Patent [19]

Boutin

[11] Patent Number: 5,056,513
[45] Date of Patent: Oct. 15, 1991

[54] MICRO-AIR-WAVE DETECTION DEVICE PARTICULARLY FOR BREATHING MONITORING AND SURVEILLANCE

[75] Inventor: Guy Boutin, Villeneuve Les Avignon, France

[73] Assignee: Revo' Air, Salon De Provence, France

[21] Appl. No.: 528,988

[22] Filed: May 25, 1990

[30] Foreign Application Priority Data

May 29, 1989 [FR] France ............................ 8907278

[51] Int. Cl.⁵ ...................... A61M 16/00; A61B 5/087
[52] U.S. Cl. .......................... 128/204.23; 128/205.23; 128/716; 128/911
[58] Field of Search ...................... 128/205.23, 204.23, 128/204.21, 716, 903, 911

[56] References Cited

U.S. PATENT DOCUMENTS

| | | | |
|---|---|---|---|
| 3,347,222 | 10/1967 | Kohrer ................................... | 128/2 |
| 3,802,417 | 4/1974 | Lang ...................................... | 128/716 |
| 3,817,238 | 6/1974 | Matson .................................. | 128/2 |
| 3,898,987 | 8/1975 | Elam ...................................... | 128/205.23 |
| 4,138,105 | 2/1979 | Hunger et al. ........................ | 128/725 X |
| 4,231,375 | 11/1980 | Boehringer et al. ................. | 128/725 |
| 4,316,182 | 2/1982 | Hodgson .............................. | 340/606 |
| 4,366,821 | 1/1983 | Wittmaier ............................ | 128/719 |
| 4,417,589 | 11/1983 | Favaloro ............................... | 128/716 |
| 4,519,387 | 5/1985 | Durkan ................................ | 128/204.23 |
| 4,570,631 | 2/1986 | Durkan ................................ | 128/204.23 |
| 4,657,025 | 4/1987 | Kohrer ................................. | 128/671 |
| 4,727,886 | 3/1988 | Conrardy et al. ................... | 128/725 |
| 4,790,811 | 12/1988 | Bloxom ................................ | 604/27 |

FOREIGN PATENT DOCUMENTS

| | | | |
|---|---|---|---|
| 1025433 | 10/1950 | France . | |
| 2053512 | 2/1981 | United Kingdom ........... | 128/205.23 |
| 8402080 | 6/1984 | World Int. Prop. O. ...... | 128/204.23 |

OTHER PUBLICATIONS

Biochem brochure, "A Complete Line of Disposables and Accessories for $CO_2$ and Apnea Monitoring".

Primary Examiner—Edgar S. Burr
Assistant Examiner—E. P. Raciti
Attorney, Agent, or Firm—Armstrong, Nikaido, Marmelstein, Kubovcik & Murray

[57] ABSTRACT

A micro air-wave detection device particularly for breathing monitoring and surveillance, which comprises a tube (2) having a ball (5) disposed therein with minimum clearance. The tube (2) is disposed in a horizontal or slightly inclined position and is connected to a conduit (38) which picks up the pressure variation of a nasal respirator (53). Detection of the to-and-fro movement of the ball at the level of an independent detection unit (10) containing the tube is transmitted by optical fibers (45) to an electronic control and alarm module (22).

21 Claims, 5 Drawing Sheets

MICRO-AIR-WAVE DETECTION DEVICE PARTICULARLY FOR BREATHING MONITORING AND SURVEILLANCE

BACKGROUND OF THE INVENTION

The invention relates to a micro air-wave detection device used more particularly for monitoring, surveilling or alerting a sleeping subject, as soon as an abnormal breathing stoppage occurs.

In the field of breathing surveillance, there already exist a number of methods and devices which unfortunately do not always give satisfactory results for the reasons given below. For persons suffering from illness or frailty, having in particular breathing difficulties or cardiac anomalies, it is necessary to monitor their sleep and possibly set off an alarm and/or oxygen supply. For that purpose, devices used must be accurate and reliable without, however, causing constraint.

The systems used up to now are based on the principle of measuring the blood pressure of the individual, or detecting movement of his rib cage, or else measuring the resistivity of the skin or the oxygen saturation of the blood. In reanimation centers, hospitals and clinics, sophisticated, heavy and cumbersome apparatus are available which require the presence of the patient and which are costly to purchase, maintain and operate. In addition, apparatus for monitoring and surveilling breathing by detection of the movement of the rib cage or the resistivity of the skin prove to be not very reliable because, in particular, the parameter for reference with respect to the movement to be measured is mobile, calibration is very difficult and finally they lack sensitivity.

Portable apparatus are preferred, for example, for measuring the arterial or venous blood pressure, or for determining the oxygen saturation of the blood. Such apparatus, however, although functioning correctly, have the enormous drawback of not being able to be used without waking the subject and without external intervention. In addition, the use of such apparatus requires that a lack of oxygen already occur in order to cause indisposition, leading to acceleration of the heart beat and a rise in blood pressure.

Finally, systems exist based on the detection of breathing itself, in which a detector is connected by a conduit to a mask or to a probe fitted to the nose of the patient, wherein the detector picks up the pressure variations in the breathing. In particular, U.S. Pat. No. 3,817,238 discloses a breathing detector for animals in which the detection member comprises a vertical transparent tube connected by a conduit to the snout of the animal. In the tube, a light ball moves at the breathing rate and its movement is detected by a photoelectric cell subjected to illumination by a light source. This system has all or nothing operation and is quite lacking in sensitivity, if only because the air pressure variation in the tube must be greater than the force of gravity which is exerted on the ball in the vertical tube.

SUMMARY OF THE INVENTION

The present invention on the contrary provides a system which is extremely sensitive to the slightest anomaly, or to the slightest discontinuity in normal breathing movement, so as to give an alarm or automatically cause the distribution of oxygen. The detection of such a small anomaly does not systematically wake up the person. The apparatus is also reliable and simple to construct and use, allowing its use under all circumstances.

The main object of the present invention consists of a micro air-wave detection device which can be used particularly for monitoring, supervising or alerting a sleeping subject as soon as an abnormal breathing stoppage occurs, comprising a conduit picking up the variations of the pressure to be monitored, connected to at least one tube containing a movable ball. The tube, with its ball, is used in a horizontal or slightly inclined position, wherein the ball moves with a minimum clearance inside the tube between two internal stops having an air passage therein. The detection of the to-and-fro movement of the ball at the level of an independent detection unit containing said tube is transmitted by a connection means to an electronic control and alarm module.

In a particular characteristic of the invention, the detection unit has passing therethrough a cylindrical opening for housing the interchangeable tube of which a central portion at least is transparent. Means are provided for positioning and locking the tube in the unit. A set of detectors is provided on each side of the tube, in alignment with the path of the ball for detecting its to-and-fro movement.

Advantageously, the means for connecting the detection unit to the electronic control and alarm module are formed of optical fiber conduits which may be formed as layers integrated in said unit.

In another particular characteristic of the invention, an oxygen intake electrovalve is fitted at the output of the pressure reducer of a cylinder, and delivers oxygen only during the breathing-in phase of the subject.

The nasal respirator used comprises two branches, one for picking up pressure variation and the other for oxygen intake, each having a nose end-piece and a mouth end-piece.

According to another characteristic of the invention, two glass tubes are used which are aligned along a slightly inclined axis and mounted in opposition to each other. The glass tubes are connected together by a flexible and sealed sleeve, having twin outlets to which a branch duct is connected and which picks up the pressure variation to be monitored.

In a variant embodiment of the invention, pressure variations are picked up by a movement sensor having a resilient and flexible membrane.

BRIEF DESCRIPTION OF THE DRAWINGS

Other complementary features, advantages and modifications of the invention will become clear from the following description of non-limitative embodiments, with reference to the accompanying drawings which show.

DETAILED DESCRIPTION OF THE PREFERRED EMBODIMENTS

Figure 1:
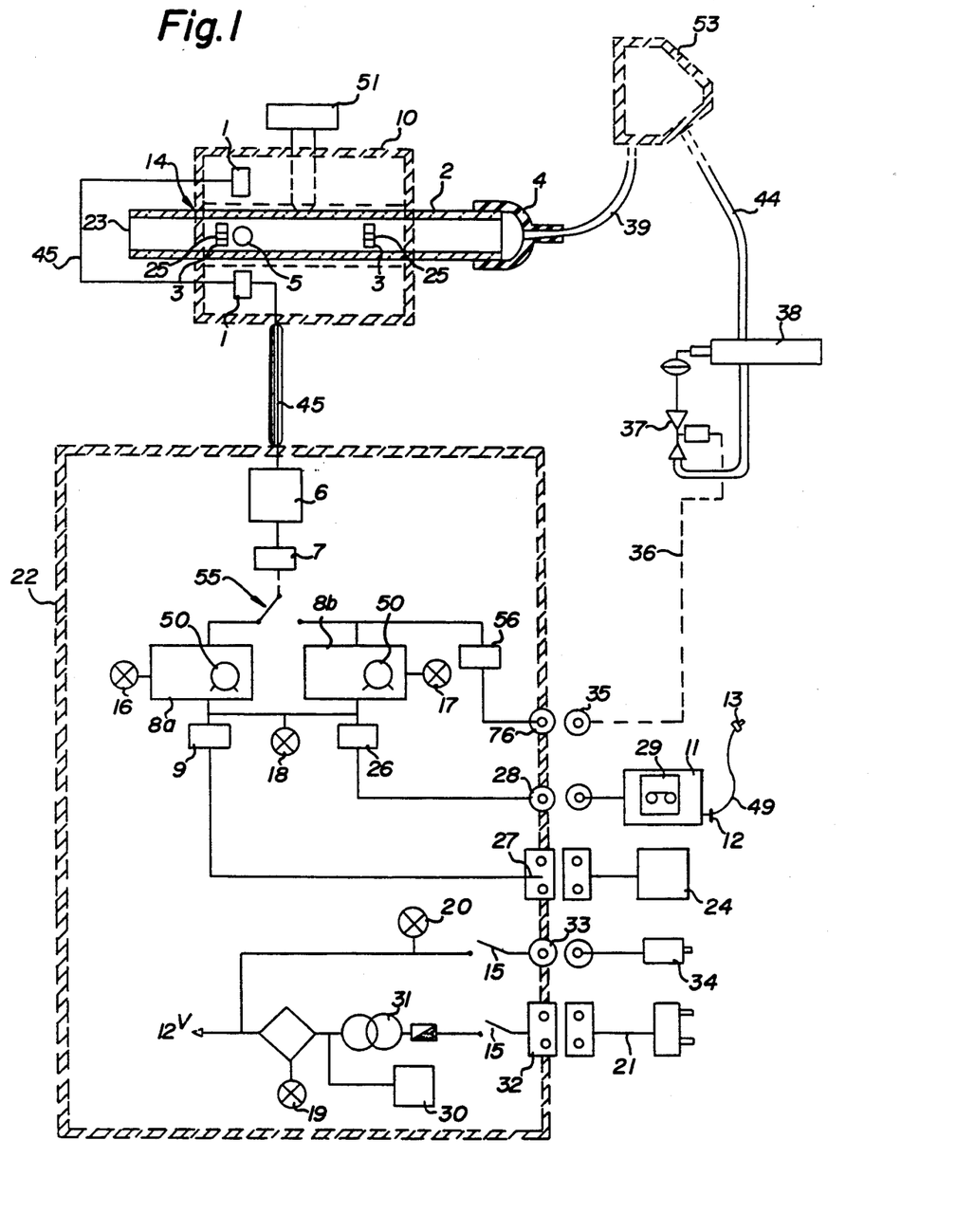
FIG. 1, a general schematic view of the detection device.

The micro air-wave detection device shown schematically as a whole in FIG. 1 comprises several basic modules: An independent detection unit 10 (also shown in FIG. 2), which is independent of an electronic control and alarm module 22 to which it is connected, and a nasal respirator designated generally by the reference number 53.

Figure 2:
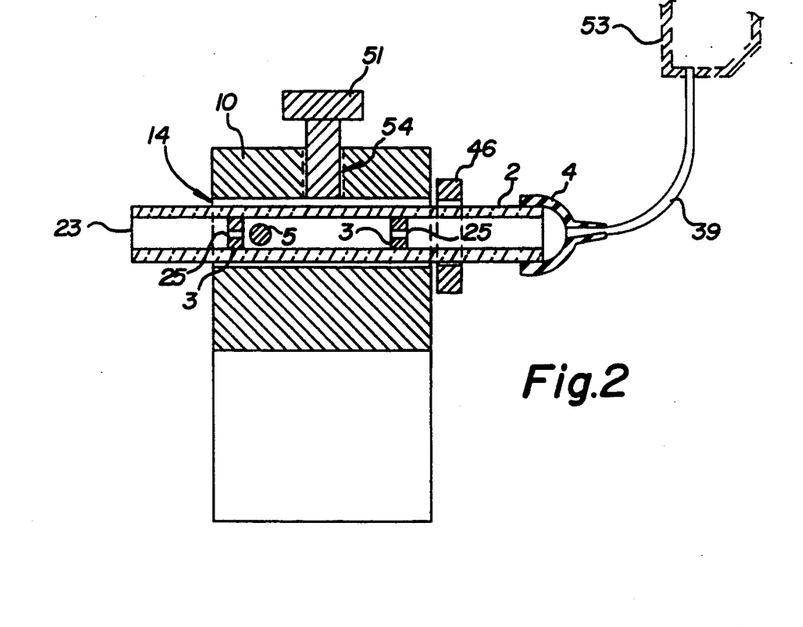
FIG. 2, a sectional view of the detection unit.

In the simplified variant shown in FIG. 2, the detection unit 10 has a horizontal cylindrical through opening 14 which serves as a housing and support for an interchangeable glass or plastic material tube 2. The tube has a central portion therein, wherein at least the central portion is transparent. Tube 2 projects on each side of the detection unit 10, and one of its ends 23 is open to the ambient atmosphere. On the other hand, its other open end is capped by a flexible sealing sleeve 4 by which the tube is connected through a small and interchangeable conduit 39 to the nasal respirator 53. An annular washer 46 is fitted on the tube 2 and serves as a positioning stop by being applied against the outer wall of the detection unit 10, thereby providing correct centering of the tube within the unit. The latter is also formed vertically with an orifice 54 which communicates with an opening 14 and in which is housed a locking screw 51 for securing the tube 2 in a correct position within the unit 10.

Inside the glass tube 2 is placed a small and very light ball 5, made for example from a plastic material or carbon fibre, and having an outer diameter which is substantially equal in diameter to the inner diameter of the tube, so that the ball may move therein with a minimum clearance. The travel of the ball within the tube is limited by two small internal stops 3 formed with a central orifice 25 or indented so as to let air pass.

It can be seen in FIG. 1 that the detection unit is equipped, on each side of the tube 2 and in the vicinity of a stop 3, with a set of detectors 1 one of which is, for example, a light source and the other a photoelectric cell. In addition, capacitive or resistive detectors may be used. In any case, the detectors are disposed so as to detect the movement of the ball 5 between the position shown, in which it occupies a position in alignment with the detectors, and another position within the tube. The detectors are connected by electric cables, or advantageously by an optical fibre conduit 45, so as to transfer the signals to the electronic control and alarm module 22. The this purpose, the conduit 45 is connected to an amplifier 6 whose output relay 7, depending on the position of a contact 55, is connected to one of two timers 8 which are adjustable by means of control knobs 50. Energization of the alarm relays 9 and 26, each corresponding to a timer, is caused by a supply voltage and controlled by an electronic circuit including the adjustable timer circuit 8, each of which receives an electric pulse from the detectors 1. When a contact of the relay 7 becomes locked in a closed or open position, depending on the chosen function, the timer begins counting in order to activate the alarm after a time pre-set by the user by means of a knob 50.

The movement of the ball 5 within the tube 2 is caused by the nasal respirator 53 which transmits, through a small diameter conduit 39, an air wave resulting from inhaling or exhaling of the subject. Detectors 1 therefore detect the to-and-fro movement of the ball 5 moving with a minimum clearance inside the tube 2 between the two stops 3.

Thus, in the event that a breathing stoppage occurs, the to-and-fro movement of the ball is halted or modified, and an alarm is given. If the subject begins breathing again, the ball takes up its to-and-fro movement again in the tube and the alarm stops. Then, the cycle begins again.

A signalling and alarm means receives the information picked up by the module 22. In particular, the applied voltage given by the contact of the alarm relay 26 may be used for supplying a sound blip transmitter 11 via a socket 28, or an earphone 13 connected to the transmitter 11, via an earphone wire with a jack 12, thereby eliminating the sound blip. Alternatively, the relay 26 may also serve for providing a cassette recording, an independent alarm, or an alarm fed by a cassette tape recorder 29. An alarm transfer may also be used remotely, which is connected to the applied voltage from the second relay 9 via an interconnection means 24 connected to the output plug 27 of the alarm module.

Furthermore, on the front face of the alarm module 22 are provided an on-off switch 15, a 220 volt socket 32 for receiving 220 V power supplied along a line 21, a light indicator 16 in connection with an adjustable timer 8a for signalling a first timing pulse, as well as another light indicator 17 in connection with the other adjustable timer 8b for signalling a second timing pulse. In addition, an alarm indicator 18 is slaved to the alarm relay (9, 26), and a control light 20 displays the state of a rechargeable battery 30 connected to a 12 volt socket connected, for example, to a vehicle cigar lighter 34 via a socket 33. For this purpose, a stabilized and filtered 220 volt/12 volt supply assembly 31, with fuses, is provided, having a 12 volt charger and control light 19 incorporated therein.

Advantageously, the detector is miniaturized for transport during travel. The detection apparatus is thus operative using an independent battery which is housed in a miniature unit which also contains the removable detection tube.

Remote supervision of the subject may be provided by retransmitting the alarm through the 220 V mains of a house, hospital or clinic, employing the same principle by which 220 V HF transmission is used for interphones. In this case, the interconnecting means 24 is used as a transmitter connected to a plug 27 receiving the 220 V supply when the alarm is tripped. A receiver tuned to the transmission frequency of the alarm of the breathing stoppage detector may be connected to any socket connected to the 220 V mains to which the detector is connected, with the output 27 driven by the relay 9.

The blip transmitter 11 or tape recorder 29, as well as the 220 V interphone-type transmitter formed of the interconnection means 24, as described above, may be incorporated in the module.

When a breathing deficiency requires an oxygen supply, a substantial savings of oxygen may be obtained with the device of the invention because the supply is only provided during the breathing-in phase of the subject. For this purpose, a 12 V output socket 76 is provided on the control module 22, for supplying, through a connector 37 and cable 36, an oxygen intake electrovalve 37 fitted at the output of the pressure reducer of a cylinder 38. The socket 76 is supplied by a relay 56 connected to the adjustable timer 8b, which is energized only by the detection of the breathing-in phase.

Figure 3:
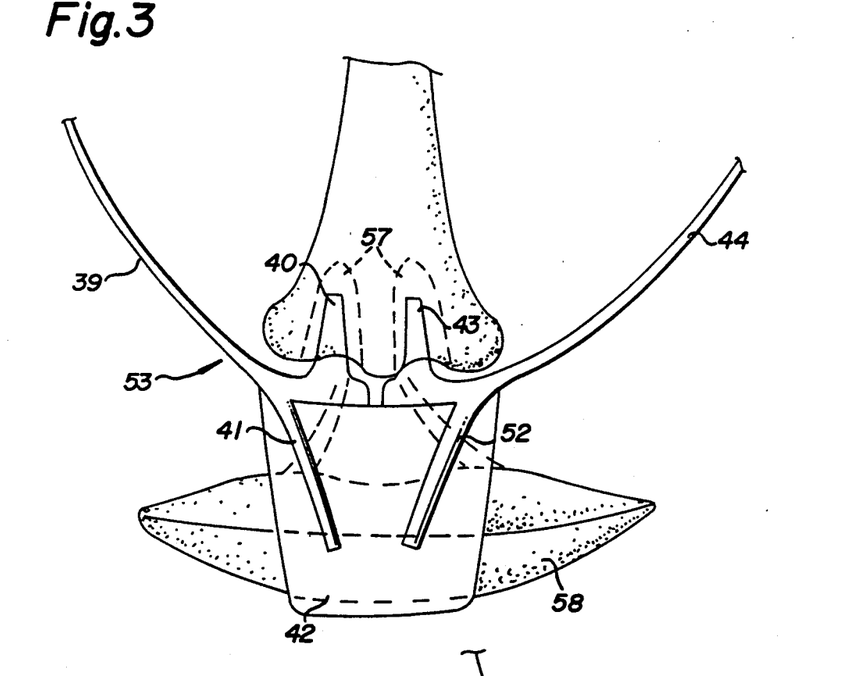
FIGS. 3 and 4, front and side views of a nasal aerator.
Figure 4:
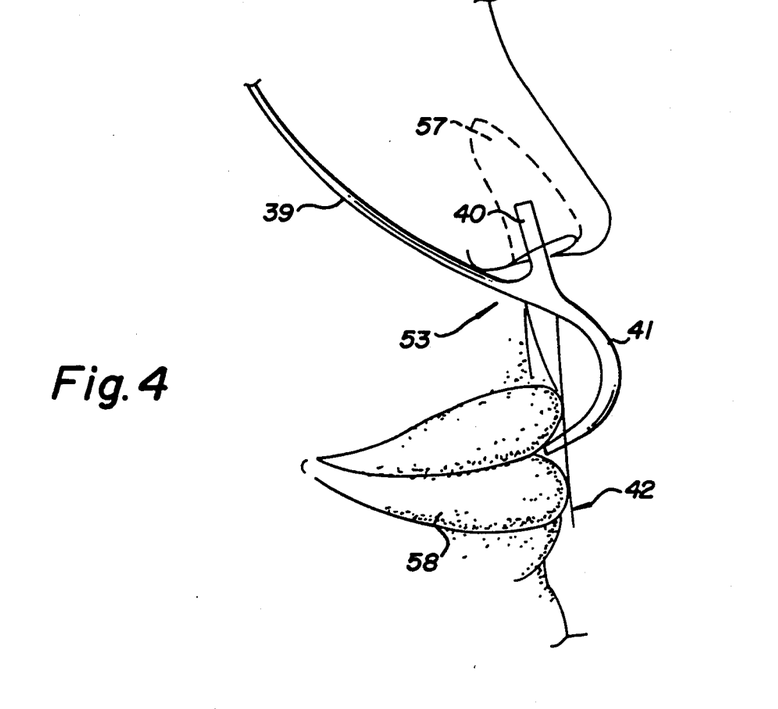
Figure 5:
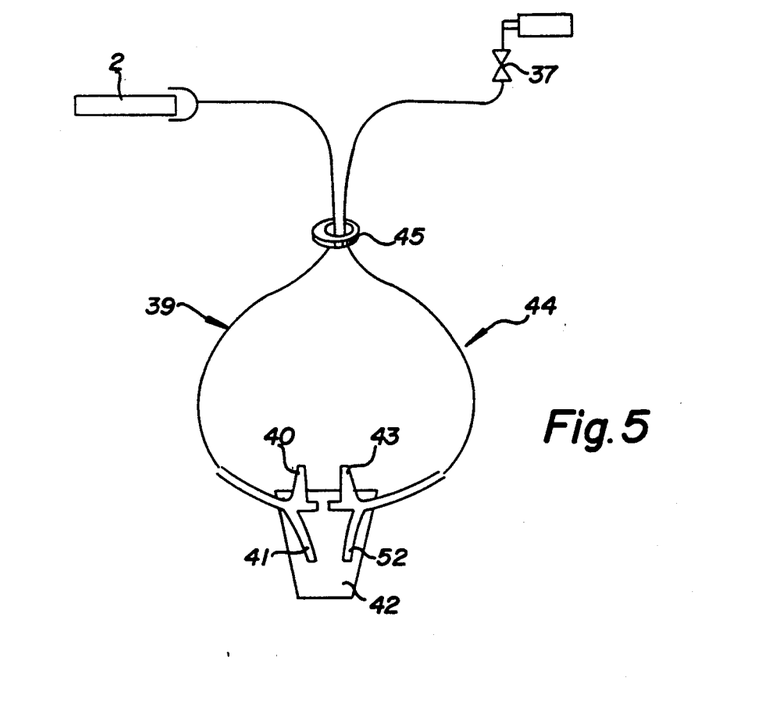
FIG. 5, a schematic view of the fitting of the nasal aerator.

The nasal respirator 53 is shown in greater detail in FIGS. 3, 4 and 5. The nasal respirator 53 has two symmetrical branches 39 and 44.

A branch 39 is connected, as mentioned above, to the tube 2 via a sleeve 4, and is divided towards nose end-pieces 40, 41 to be introduced into the nostrils 57 of the subject, and also branching off to a mouth end-piece, to be introduced into the mouth 58 of the subject. The end of the branch 39 with its end-pieces 40, 41 is fixed to a flat and flexible support 42 which is pierced so that the mouth end-piece 41 receives the inhaled and exhaled air of a subject sleeping occasionally with his mouth open. A support 42 is laid astride the closed lips of the subject.

The other branch 44 of the nasal respirator 53 is connected to the output of the electrovalve 37 (FIG. 1) which provides oxygen distribution. This branch also ends in a nose end-piece 43 penetrating into the other nostril, as well as another branching off mouth end-piece 52. The branch 44 and its end-pieces 43 and 52 are also fixed similarly to the flat and flexible support 42. The positioning of the nose end-piece and the mouth end-piece is therefore correctly obtained. A plastic sliding ring 45 clamps the two branches 39 and 44 behind the head, for holding the nasal respirator in position, as can be seen more clearly in FIG. 5.

In FIG. 3, it can be seen that the two branches 39 and 40 of the nasal respirator 53 are independent of each other since they are connected to different circuits.

Figure 7:
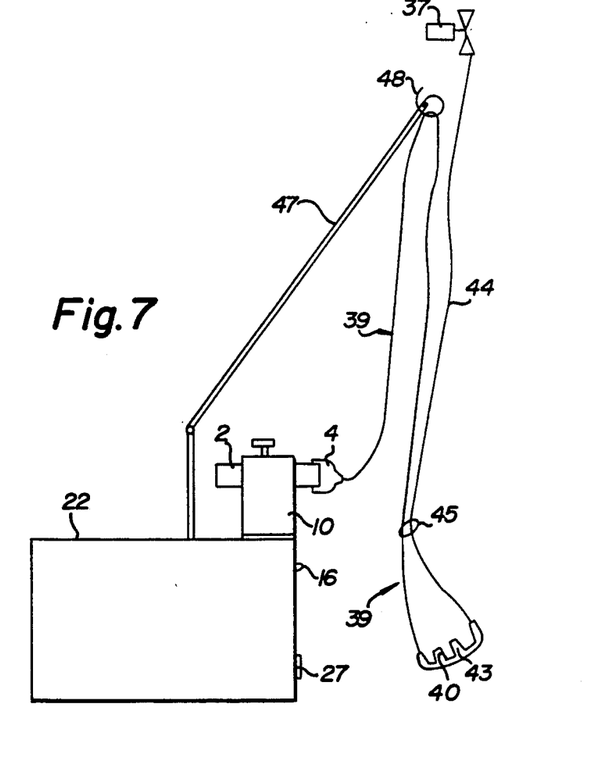

In a variant embodiment, the two nose end-pieces 40 and 43 are connected to the two branches 39 and 40, which are then placed in communication for using the nose end-piece assembly either for breathing-in detection or for blowing oxygen continuously, as shown more precisely in FIG. 7.

In yet another variant, not shown, for permitting both detection and oxygen-therapy, the mask could be formed of double nose and mouth end-pieces, corresponding to separate circuits.

Figure 6:
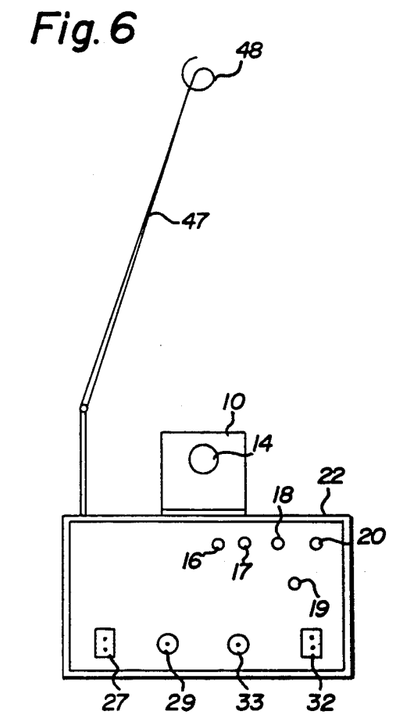
FIGS. 6 and 7, front and side views of the detection device.

FIGS. 6 and 7 illustrate a particular embodiment of the micro air-wave detection device described above. The electronic control and alarm module 22 comprises a casing having the different above-mentioned sockets or indicator lights on one of its faces. The detection unit 10 is disposed above the module equipped with the tube 2.

An articulated telescopic support 47 is retractably fixed to the module 22, having an upper end which terminates in a ring 48, referred to as a "pig's tail," and in which the flexible tubes 39 and 44 of the nasal aerator are engaged. Additional wires, such as the earphone wire 49 for listening by ear or by headphone, may also be disposed therein. These tubes and wires are therefore held in position by the ring at a height which cannot disturb the sleeping subject. It will be noted that the unit 10 is independent and could be placed elsewhere, even at a certain distance from the module 22, since in any case it is connected to the module only by a conduit 45 formed advantageously from optical fibers.

Figure 10:
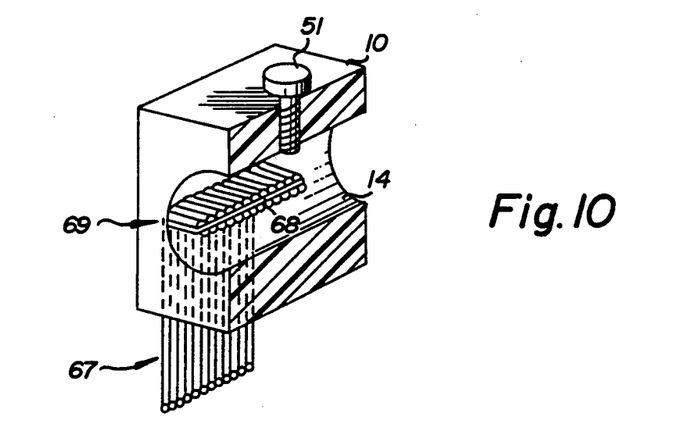
FIG. 10, a partial schematic view in perspective of a similar detection block.

In order to transmit the information by optical fibers, a similar detection block is advantageously used, such as that shown in FIG. 10.

The block 10 also has an opening 14 passing therethrough for housing the glass tube, not shown, held in position by locking screws 51. A layer 67 of optical fibers 45, including a portion 69 bent at 90 degrees, is embedded in the mass of the block and opens through a longitudinal aperture 68 into the cavity formed by an opening 14. Another layer of optical fibers, symmetrical with the first, but not shown for sake of clarity of the figure, opens into the front through another longitudinal aperture. Thus, on one side is located a series of light-emitting fibers and on the other side a series of receiving fibers is connected to the module 22.

In a variant embodiment, the optical fibers could be replaced by a shape recognition device formed for example of strips of sensitive cells associated with an artificial intelligence device.

Furthermore, the take-off element for detecting breathing is formed by a sealed sleeve 4 fitted over the tube 2, which is connected by a conduit 39 to the nasal aerator 53. The aerator 53 may therefore be at a great distance from the subject. In fact, the conduit 39 is of a small cross section, and hence the volume of air contained therein is small. Even a conduit 39 having a great length would not disturb the micro air-waves generated by the subject. This is an interesting advantage which allows the device to be used under particular conditions, for example, for use with persons working or moving in a dangerous or explosive atmosphere. In particular, the invention makes possible the remote monitoring of the regularity of breathing, for bringing help in the case of a breathing anomaly.

The invention has been described on the basis of a simplified version thereof comprising a detection unit such as that illustrated in FIG. 2, in which the tube 2 is disposed in a horizontal position. However, the invention is not limited to this particular variant, but also encompasses a construction of the unit in which the tube is in a slightly inclined position, the word "slightly" defining a slope which just sufficient and necessary so that the force of gravity can be exerted on the light ball 5, against inertia and friction forces due to its small clearance within the tube, so that the ball falls back under its own weight to the low part of the inclined tube when it is no longer subjected to the inhaling or exhaling of the subject. With a small inclination of the glass tube, the ball 5 does not stick to one or another of the stops 3 because it is applied on a stop during each inhale and exhale of the subject. Furthermore, the sensitivity of the apparatus is thereby increased, which allows the device to be calibrated.

Figure 8:
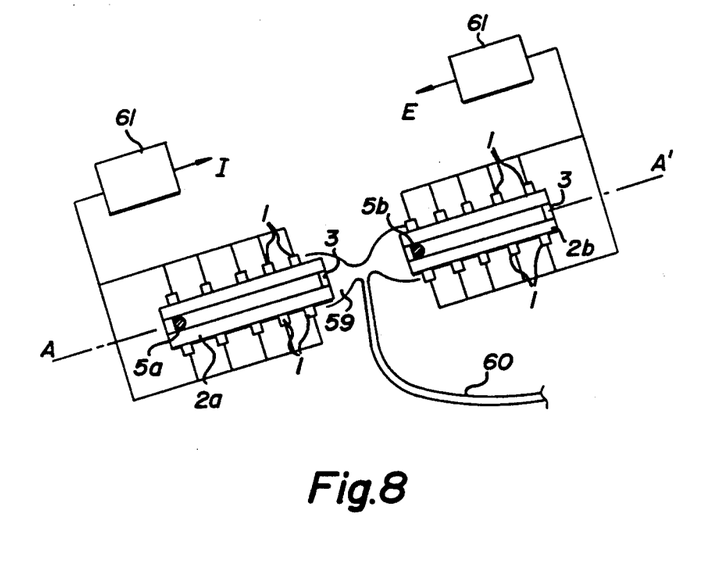
FIG. 8, a variant construction of the detection unit.

To better understand the operation of the device with an inclined tube, a particular embodiment will be described hereafter with reference to FIG. 8.

Two glass tubes 2a and 2b, which are aligned along an axis AA' which is adjustably inclined with respect to the horizontal, are connected together by a flexible sealing sleeve 59 having a dual output, on which a branch conduit 60 connects the two tubes to the nasal respirator. Each tube is also equipped with stops 3. Several sets of opto-electronic detectors 1 or optical fiber layers are disposed along each tube, each detector being connected to an electronic unit 61 for storing the position of the ball 5 in each tube.

In this device, with two inclined tubes mounted in opposition, gravity holds the ball in the low position as shown, i.e. wherein the ball 5a is on the same side as the open end of the tube 2a, whereas the ball 5b is at the side of the sleeve 59 in tube 2b. When the subject breathes in through tube 60, the ball 5b will remain motionless, but ball 5a will rise in the glass tube 2a over a length proportional to the breathing intensity, so as to come against the top stop at a maximum. The length of movement of the ball will be detected by the corresponding detector. On the other hand, on breathing out, the ball 5a will come back to its first position under the effect of the air wave and gravity, wherein ball 5b will remain pushed back in the glass tube 2b over a length proportional to the intensity of exhaled breathing, wherein the length of movement is also detected by the corresponding detector. Thus, at the output of the electronic unit 61 corresponding to the tube 2a which reacts to inhaling I of the subject, and at the output of the other unit 61 corresponding to the tube 2b which reacts to exhaling E of the subject, an analog or digital signal is obtained which can be supplied to the interface input of a computer or other appropriate measuring apparatus for recording, monitoring and measuring both the exhaled breathing rate and also the inhaled breathing rate. A curve or graph may then be obtained for determining the rib cage volume, as well as the ventilatory actions of the breathing organs, particular for measuring small breathing rates in the case of detection of hypopnea.

This embodiment is extremely sensitive to the least micro air wave established in the conduit 60, all the more so since the series of sensors 1 makes it possible to monitor the slightest movement of the ball 5 which, as described above, is very light and moves with a small clearance. The conduit in question may also be connected to a detection system other than the above-described nasal respirator. Thus, using the assembly of FIG. 8, the movement of the heart could be detected by detecting the movement of the thorax or abdomen, or the beat of an artery, provided that a very sensitive sensor is used, in place of the nasal respirator, for generating a micro air-wave.

Figure 9:
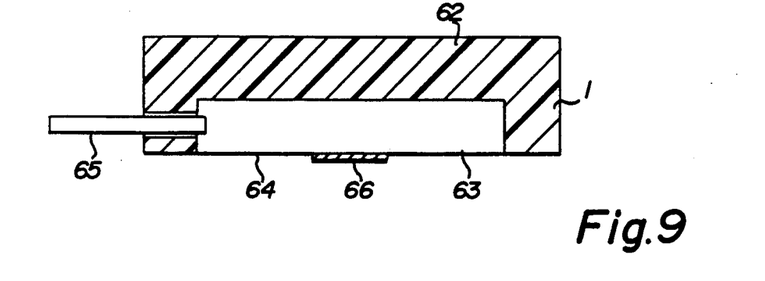
FIG. 9, a movement sensor variant.

For this purpose, in another variant, the invention provides a movement sensor such as that shown in FIG. 9.

The sensor in question is formed of a rigid annular body 62 forming a flat case having an internal chamber 63 which is closed by a thin, resilient and flexible membrane 63 advantageously made from rubber or a similar material. The body 62 is formed with an orifice equipped with a collecting tube 65 on which the above-mentioned flexible conduit 60 will be fitted leading to the inclined tubes, so as to cause the chamber 63 to communicate with the inclined tubes. A small permanent magnet 66 may also be fixed on the membrane 64. The purpose of the magnet 66 will be described below.

With the membrane stretched over the sensor, such as a stethoscope, the membrane is applied to a portion of the body, wherein a small beat or movement of the body creates a pressure or depression within the chamber 63. Thus, the deformation of the resilient membrane 64, owing to the connection 60, causes a to-and-fro movement of the balls within the glass tubes.

This sensor may also be used as an electronic switch, or as an electronic magnetic switch, because of the permanent magnet 66, thereby allowing the detection of metal objects without direct contact of the sensor with such objects.

Figure 11:
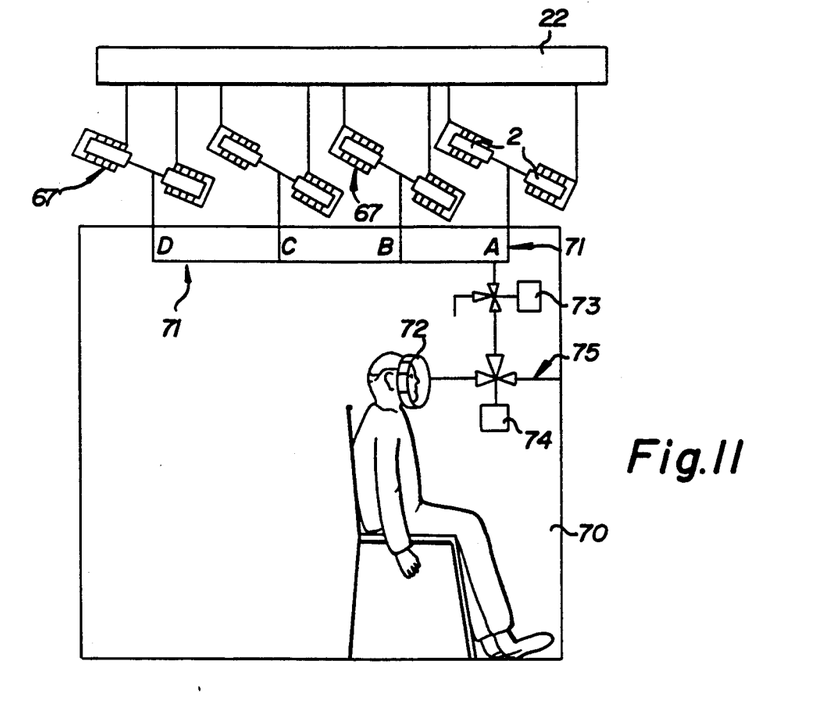
FIG. 11, a schematic diagram of the apparatus for use in examination of a patient in a closed enclosure.

Such a detection device may also be used for functional examination of breathing in an enclosure, as illustrated in FIG. 11.

In a perfectly sealed enclosure 70, inside which is placed the subject to be examined, connection tubes 71 are connected from four sets A, B, C, D of twin measuring tubes 2 with adjustable inclination. Tubes 71 are connected to a sealed breathing mask 72 worn by the subject, via two three-way electrovalves 73 and 74. The electrovalve 73 is provided for selecting measurement of the rib cage expansion, whereas the three-way electrovalve 74 is provided for selecting the measurement of the real volume breathed in an out through a tube in direct communication with the outside.

Each tube 2 is equipped with a layer 67 of optical fibers connected to a module 22 providing amplification and allowing integration of the analog and measurement signals. Each set A, B, C, D of inclined tubes is calibrated, for example by causing the inclination of one or more tubes to vary, so as to correspond with a given level of the measured breathing rates. Thus, the real volume breathed in and out may be measured by direct communication of the breathing of the subject which passes completely through the four measurement scales.

Finally, by combining one or more of the above thoracic or abdominal sensors with a nose or mouth sensor, both the breathing rate and the breathing volume of a subject may be readily measured and monitored.

It can be readily understood that the above-described micro air-wave detection devices find particular applications in the field of breathing monitoring and surveillance. However, the invention is not limited to these specific uses, and thus various uses employing the inventive device for detecting movement of micro air-waves by means of a horizontal or slightly inclined tube also form part of the present invention.

I claim:
1. A micro air-wave detection device for monitoring or alerting a sleeping subject as soon as an abnormal breathing stoppage occurs, comprising:
   a detection unit housing a transparent tube disposed in a horizontal or slightly inclined position;
   a movable ball disposed in said transparent tube, the diameter of said ball being slightly less than an internal diameter of said tube so that said ball moves inside said tube with a minimum clearance between said ball and an internal wall of said tube;
   a conduit connected at one end thereof to said transparent tube for conveying pressure variations to said tube;
   two internal stops disposed respectively at opposite ends of said tube for retaining said ball inside said tube, said internal stops having respective air passages therein;
   detector means disposed adjacent said tube for detecting a to-and-fro movement of said ball within said tube;
   electronic control and alarm means for emitting an alarm when said abnormal breathing stoppage occurs, said electronic control and alarm means receiving a signal from said detection means, said signal being transmitted though a signal line connecting said detector means and said electronic control and alarm means.

2. A detection device according to claim 1, further comprising a cylindrical opening passing through said detection unit, wherein said transparent tube is interchangeably disposed in said opening, and further comprising a locking means for positioning and locking said tube in said detection unit.

3. A detection device according to claim 1, wherein said internal stops have central orifices therein defining said respective air passages.

4. A detection device according to claims 1 or 2, wherein said detector means comprises at least one set of detectors disposed on each side of said tube, said set of detectors being aligned along said tube.

5. A detection device according to claim 1, wherein said signal line comprises optical fiber conduits.

6. A detection device according to claim 2, wherein said detection unit comprises a detection block having two rows of optical fibers embedded therein, wherein said rows of optical fibers are disposed in longitudinal apertures defined in said block such that said optical fibers face each other across said cylindrical opening.

7. A detection device according to claim 1 or 5, wherein said electronic control and alarm means comprises at least two adjustable timers, said adjustable timers being connected to respective alarm relays, wherein said alarm relays are energized in response to pulses generated by said detector means, further comprising signaling and alarm means, connected to said electronic control and alarm means, for emitting a signal and/or alarm in response to an output from said alarm relays.

8. A detection device according to claim 7, wherein said electronic control and alarm means comprises respective light indicators connected to each of said adjustable timers, an alarm indicator light connected to said signaling and alarm means for indicating an alarm state, and a battery charging control light for indicating a charging state of a battery.

9. A detection device according to claim 7 wherein said electronic control and alarm means comprises an alarm sound blip transmitter, said sound blip transmitter comprising a cassette recorder.

10. A detection device according to claim 1, further comprising transmitter means for remote transmission of said alarm to a receiver at a prescribed frequency, said transmitter means receiving a 220 V power supply after tripping of said alarm.

11. A detection device according to claim 1, further comprising an oxygen containing tank having a pressure reduction means fitted at an output thereof, and further comprising an oxygen intake electrovalve means fitted at an output of said pressure reducer for delivering oxygen to the subject only during a breathing-in phase of the subject.

12. A detection device according to claim 11, further comprising a nasal respirator having two branches connected thereto, wherein one of said branches is connected to said oxygen intake electrovalve, and the other of said branches is connected to said transparent tube via said conduit, wherein said conduit conveys pressure variations from said nasal respirator to said tube.

13. A detection device according to claim 12, wherein each of said two branches respectively comprises a nose end-piece and a mouth end-piece.

14. A detection device according to claim 13, further comprising a support means for supporting said two branches such that, when said support means is laid across the lips of the subject, said nose end-pieces and said mouth end-pieces are positioned, respectively, proximate the nostrils and mouth of said subject.

15. A detection device according to claim 13, wherein said nose end-pieces are connected to said respective branches and are in communication with each other, wherein oxygen can be supplied or breathing can be detected through both of said nose-end pieces.

16. A detection device according to claim 1, wherein said conduit has a small internal diameter and a length for allowing said conduit to convey said pressure variations from a distance.

17. A detection device according to claim 1, wherein said transparent tube comprises two glass tubes mounted such that said glass tubes are both aligned along a slightly inclined axis and wherein respective ends of said glass tubes oppose each other along said axis, said glass tubes being connected together at said respective ends by a sealed sleeve, said conduit comprising a branch duct connected to said sleeve for conveying pressure variations to said glass tubes.

18. A detection device according to claims 1 or 17, further comprising a movement sensor means connected to an opposite end of said conduit, wherein said movement sensor means comprises a resilient and flexible membrane disposed over a closed chamber, said conduit being connected to said closed chamber, wherein movement of said membrane causes an air wave to be formed in said chamber and conveyed along said conduit to said transparent tube.

19. A detection device according to claim 18, further comprising a permanent magnet disposed on said flexible membrane.

20. A detection device according to claims 1 or 17, further comprising a plurality of transparent tubes connected by respective conduits to an enclosure containing said subject.

21. A detection device according to claims 1 or 17, further comprising a means for measuring the heart rate and/or blood oxygenation of said subject.

* * * * *